US008795517B2

(12) United States Patent
Lannoy

(10) Patent No.: US 8,795,517 B2
(45) Date of Patent: *Aug. 5, 2014

(54) MACHINE READABLE MEDIUM EMBODYING INSTRUCTIONS FOR CITRATE ANTICOAGULATION SYSTEM FOR EXTRACORPOREAL BLOOD TREATMENTS

(71) Applicants: Baxter International Inc., Deerfield, IL (US); Baxter Healthcare S.A., Glattpark (CH)

(72) Inventor: Jean-Michel Lannoy, Anstaing (FR)

(73) Assignee: Nikkiso Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/960,234

(22) Filed: Aug. 6, 2013

(65) Prior Publication Data

US 2013/0323122 A1 Dec. 5, 2013

Related U.S. Application Data

(60) Division of application No. 13/359,109, filed on Jan. 26, 2012, now Pat. No. 8,529,486, which is a division (Continued)

(30) Foreign Application Priority Data

Apr. 26, 1999 (EP) ..................................... 99201302

(51) Int. Cl.
*A61M 1/34* (2006.01)
*B01D 61/32* (2006.01)
*B01D 61/28* (2006.01)
*B01D 61/30* (2006.01)

(52) U.S. Cl.
USPC ................ 210/134; 210/85; 210/86; 210/87; 210/90; 210/97; 210/102; 210/103; 210/143; 210/149; 210/175; 210/252; 210/257.1; 210/257.2; 210/258; 604/4.01; 604/5.01; 604/5.04; 604/6.07; 604/6.09; 604/6.11; 604/19; 604/28; 604/30; 604/65

(58) Field of Classification Search
USPC ......... 210/645, 646, 650, 739, 741, 742, 744, 210/85, 86, 87, 90, 97, 102, 103, 134, 143, 210/149, 175, 252, 257.1, 257.2, 258; 604/4.01, 5.01, 5.04, 6.07, 6.09, 6.11, 604/19, 28, 30, 65
See application file for complete search history.

(56) References Cited

U.S. PATENT DOCUMENTS 3,962,075 A 6/1976 Fialkoff et al.
(Continued)

FOREIGN PATENT DOCUMENTS

DE 4122754 1/1993
(Continued)

OTHER PUBLICATIONS

Macias, W.L.; "Choice of replacement fluid/dialysate anion in continuous renal replacement therapy"; American Journal of Kidney Diseases, (1996) 28/5 Suppl. 3 (S1 5-S20); XP000978102; Abstract; p. S15-p. S16; p. S19.
(Continued)

*Primary Examiner* — John Kim
(74) *Attorney, Agent, or Firm* — Oliff PLC

(57) ABSTRACT

A machine-readable medium with instructions for pumping blood from a patient's blood stream into an access line, introducing an anticoagulant solution into the pumped blood, filtering the pumped blood and delivering it to a return line, introducing a substitution fluid into the pumped blood, introducing a calcium and magnesium solution into the blood traveling through the return line, and returning the blood back to the patient's blood stream.

11 Claims, 6 Drawing Sheets

Related U.S. Application Data of application No. 11/602,827, filed on Nov. 21, 2006, now Pat. No. 8,105,258, and a continuation-in-part of application No. 10/742,137, filed on Dec. 19, 2003, now Pat. No. 7,186,420, which is a continuation-in-part of application No. 09/959,543, filed as application No. PCT/EP00/03583 on Apr. 20, 2000, now Pat. No. 6,743,191.

(60) Provisional application No. 60/739,086, filed on Nov. 22, 2005.

(56) References Cited

U.S. PATENT DOCUMENTS

| | | | |
|---|---|---|---|
| 4,308,255 A | 12/1981 | Raj et al. |
| 4,336,881 A | 6/1982 | Babb et al. |
| 4,339,433 A | 7/1982 | Kartinos et al. |
| 4,489,535 A | 12/1984 | Veltman |
| 4,574,085 A | 3/1986 | Dolkart et al. |
| 4,604,379 A | 8/1986 | Twardowski et al. |
| 4,649,050 A | 3/1987 | Veech |
| 4,663,166 A | 5/1987 | Veech |
| 4,668,400 A | 5/1987 | Veech |
| 4,690,772 A | 9/1987 | Tell et al. |
| 4,711,715 A | 12/1987 | Polaschegg |
| 4,879,280 A | 11/1989 | Seyffart et al. |
| 4,880,629 A | 11/1989 | Okamoto et al. |
| 4,886,789 A | 12/1989 | Milner |
| 4,889,634 A | 12/1989 | El-Rashidy |
| 4,980,374 A | 12/1990 | Steudle et al. |
| 5,011,826 A | 4/1991 | Steudle et al. |
| 5,032,615 A | 7/1991 | Ward et al. |
| 5,100,677 A | 3/1992 | Veech |
| 5,178,763 A | 1/1993 | Delaunay |
| 5,192,459 A | 3/1993 | Tell et al. |
| 5,211,643 A | 5/1993 | Reinhardt et al. |
| 5,252,213 A | 10/1993 | Ahmad et al. |
| 5,296,242 A | 3/1994 | Zander |
| 5,366,630 A | 11/1994 | Chevallet |
| 5,436,232 A | 7/1995 | Forster et al. |
| 5,589,197 A | 12/1996 | Shockley et al. |
| 5,597,805 A | 1/1997 | Breborowicz et al. |
| 5,616,248 A | 4/1997 | Schal |
| 5,626,880 A | 5/1997 | Inoue et al. |
| 5,629,025 A | 5/1997 | Shockley et al. |
| 5,631,025 A | 5/1997 | Shockley et al. |
| 5,670,176 A | 9/1997 | Martis et al. |
| 5,674,527 A | 10/1997 | Inoue et al. |
| 5,698,230 A | 12/1997 | Martis et al. |
| 5,728,681 A | 3/1998 | Kido et al. |
| 5,762,805 A | 6/1998 | Truitt et al. |
| 5,827,820 A | 10/1998 | duMoulin et al. |
| 5,910,252 A | 6/1999 | Truitt et al. |
| 5,945,129 A | 8/1999 | Knerr et al. |
| 5,945,449 A | 8/1999 | Purcell et al. |
| 5,955,450 A | 9/1999 | Breborowicz et al. |
| 6,017,942 A | 1/2000 | Bergstrom |
| 6,020,007 A | 2/2000 | Veech |
| 6,077,836 A | 6/2000 | Milner |
| 6,083,935 A | 7/2000 | Wu et al. |
| 6,156,797 A | 12/2000 | Kubo et al. |
| 6,200,485 B1 | 3/2001 | Kitaevich et al. |
| 6,214,802 B1 | 4/2001 | Nakamura et al. |
| 6,248,726 B1 | 6/2001 | Alsop et al. |
| 6,251,437 B1 | 6/2001 | Fischbach |
| 6,277,556 B1 | 8/2001 | Grode et al. |
| 6,277,815 B1 | 8/2001 | Knerr |
| 6,306,836 B1 | 10/2001 | Martis et al. |
| 6,309,673 B1 | 10/2001 | Duponchelle et al. |
| 6,610,206 B1 | 8/2003 | Callan et al. |
| 6,730,233 B2 | 5/2004 | Pedrazzi |
| 6,743,191 B1 | 6/2004 | Chang |
| 6,814,864 B1 | 11/2004 | Favre et al. |
| 7,186,420 B2 | 3/2007 | Chang et al. |
| 2001/0003794 A1 | 6/2001 | Landry et al. |
| 2004/0129638 A1 | 7/2004 | Chang et al. |
| 2005/0011823 A1 | 1/2005 | Delnevc et al. |
| 2008/0154170 A1 | 6/2008 | Lannoy |

FOREIGN PATENT DOCUMENTS

| | | |
|---|---|---|
| DE | 4211455 | 12/1993 |
| DE | 19654746 | 12/1996 |
| EP | 076355 | 4/1983 |
| EP | 086553 | 8/1983 |
| EP | 0115911 | 8/1984 |
| EP | 0153164 | 8/1985 |
| EP | 0399918 | 11/1990 |
| EP | 0417478 | 3/1991 |
| EP | 0456928 | 11/1991 |
| EP | 0532432 | 9/1992 |
| EP | 0602014 | 6/1994 |
| EP | 0821951 | 2/1998 |
| GB | 2084484 | 4/1982 |
| JP | 356010109 | 2/1981 |
| JP | 56 128711 | 10/1981 |
| JP | 01242531 | 9/1989 |
| JP | 403038527 | 2/1991 |
| JP | 04069341 | 3/1992 |
| JP | 405105633 | 4/1993 |
| JP | 406105906 | 4/1994 |
| JP | 406178802 | 6/1994 |
| JP | 406237991 | 8/1994 |
| JP | 406245995 | 9/1994 |
| JP | 406335527 | 12/1994 |
| JP | 406335528 | 12/1994 |
| JP | 407059846 | 3/1995 |
| JP | 408092071 | 4/1996 |
| JP | 408131542 | 5/1996 |
| JP | 408164199 | 6/1996 |
| JP | 408169836 | 7/1996 |
| JP | 410087478 | 4/1998 |
| JP | 411114054 | 4/1999 |
| JP | 411197240 | 7/1999 |
| JP | 11279051 | 10/1999 |
| JP | 411343230 | 12/1999 |
| JP | 02000037452 | 2/2000 |
| JP | 02000051348 | 2/2000 |
| JP | 02000072658 | 3/2000 |
| JP | 02000140095 | 5/2000 |
| JP | 02000245826 | 9/2000 |
| JP | 02000288083 | 10/2000 |
| JP | 02001054570 | 2/2001 |
| WO | WO 90/15612 A | 12/1990 |
| WO | WO 91/10457 | 7/1991 |
| WO | WO 93/19792 | 10/1993 |
| WO | WO 93/24108 | 12/1993 |
| WO | WO 96/01118 | 1/1996 |
| WO | WO 97/30694 | 8/1997 |
| WO | WO 98/10745 | 3/1998 |
| WO | WO 98/29151 | 7/1998 |
| WO | WO 98/50091 | 11/1998 |
| WO | WO 99/01144 | 1/1999 |
| WO | WO 99/09953 | 3/1999 |
| WO | WO 99/17762 | 4/1999 |
| WO | WO 99/20249 | 4/1999 |
| WO | WO 00/33853 | 6/2000 |
| WO | WO 2004/069311 | 8/2004 |

OTHER PUBLICATIONS

Ono, K., et al.; "Glucose in the dialyzate does not reduce the free amino acid loss during routine hemodialysis of non-fasting patients"; Clinical Nephrology, (1984) 21/2 (106-109); Coden: CLNHBI; XP000856986; Abstract.

Palsson, R., et al.; "Regional citrate anticoagulation in continuous venovenous hemofiltration in critically ill patients with a high risk of bleeding"; Kidney International, (May 1999) 55 (5); 1991-7; XP000978115, Abstract.

(56) References Cited

OTHER PUBLICATIONS

Sieberth, H.G.; ["Composition of the rinsing water for extracorporeal hemodialysis in acute and chronic renal failure"]; Zusammensetzung des Waschwassers fur die extracorporale Hamodialyse der akuten and chronischen Niereninsuffizienz; Medizinische Technik, (1974) 94/2 (28-32); Coden Meteav; XP000856013; Abstract, p. 31, col. 2, Table 1.

Van Stone, J.C.; "Individualiation of the dialysate prescription in chronic hemodialysis", Dialysis and Transplantation (1994) 23/11 (624-625+628-635) XP000856008; Abstract the Whole Document, p. 634.

MACHINE READABLE MEDIUM EMBODYING INSTRUCTIONS FOR CITRATE ANTICOAGULATION SYSTEM FOR EXTRACORPOREAL BLOOD TREATMENTS

CROSS REFERENCE TO RELATED APPLICATIONS

This application is a division application of U.S. patent application Ser. No. 13/359,109, filed Jan. 26, 2012, now U.S. Pat. No. 8,529,486, which is a division application of U.S. patent application Ser. No. 11/602,827, filed Nov. 21, 2006, now U.S. Pat. No. 8,105,258, which claims benefit of priority from U.S. Provisional Patent Application Ser. No. 60/739,086, filed Nov. 22, 2005. U.S. patent application Ser. No. 11/602,827 is also a continuation-in-part of related U.S. patent application Ser. No. 10/742,137, filed Dec. 19, 2003, now U.S. Pat. No. 7,186,420, which is a continuation-in-part of U.S. patent application Ser. No. 09/959,543, filed Oct. 23, 2001, now U.S. Pat. No. 6,743,191, which is a Section 371 filing of PCT/EP00/03583, filed Apr. 20, 2000, which claims priority to EP 99201302.9, filed Apr. 26, 1999, the entire contents of which are all herein incorporated by reference in their entirety.

FIELD OF THE INVENTION

The invention relates generally to extracorporeal blood treatment systems. More particularly, the invention relates to a citrate anticoagulation treatment for an extracorporeal blood treatment system capable of introducing various solutions into the blood to assist in the filtering of the blood.

DESCRIPTION OF THE RELATED ART

Extracorporeal blood treatment is a therapy that is widely used for critically ill patients. Many of these patients suffer from acute renal failure and are treated with various forms of hemofiltration, such as Continuous Renal-Replacement Therapy (CRRT), Continuous Veno-Venous Hemofiltration (CVVH), Continuous Arterio-Venous Hemofiltration (CAVH), and Continuous Veno-Arterial Hemofiltration (CVAH).

Another form of renal replacement therapy that can be used for patients with renal failure in Intensive Care Units (ICU's) is hemodialysis. Pure hemofiltration, as a renal-replacement therapy in an ICU, can be combined with hemodialysis to provide a Continuous-Veno-Venous-Hemo-DiaFiltration (usually abbreviated as CVVHD or CVVHDF) or a Continuous-Arterio-Venous-Hemo-DiaFiltration (usually abbreviated as CAVHD or CAVHDF). The addition of hemodialysis to a hemofiltration therapy allows the infusion of a hemodialysis fluid, such as a dialysate fluid, making such combined therapy forms more complex than pure hemofiltration. Hemodialysis usually can only be applied for a few hours per day, and as such, is much less effective than pure hemofiltration.

Typically, an artificial kidney is used for extracorporeal treatments. This kidney may be formed of hollow-fibers or of plates, and is connected to a patient's bloodstream by an extracorporeal circuit. In CVVH(D) the supply from and return to the blood of the patient is made via two venous accesses, using a blood pump to provide the driving force for the transport of blood from the patient into the artificial kidney and back to the patient. In CAVH(D), the access which provides the supply of blood to the artificial kidney is made via an artery and the return of the blood to the patient is made via a venous access. In most cases, blood pumps are generally not used because the arterial blood pressure is used to provide the driving force for the transport of blood, which implies that the blood flow rate directly varies with the blood pressure. Because of better control of blood flow, no risk of arterial catheter-related complications, and higher treatment efficiency, CVVH is a preferred renal replacement therapy in ICU's over CAVH.

In CVVH, the patient's blood is passed through the artificial kidney over a semipermeable membrane. The semipermeable membrane selectively allows plasma water and matter in the blood to cross the membrane from the blood compartment into the filtrate compartment, mimicking the natural filtering function of a kidney. This leads to a considerable loss of fluid from the blood, which is removed as the filtrate in the artificial kidney. Every liter of filtrate fluid that is removed in the artificial kidney, contains a large fraction of the molecules that are dissolved in the plasma, like urea, creatinine, phosphate, potassium, sodium, glucose, amino acids, water-soluble vitamins, magnesium, calcium, sodium, and other ions, and trace elements. The fraction of the molecules that passes the semipermeable membrane depends mainly on the physico-chemical characteristics of the molecules and the membrane. In order to keep the blood volume of the patient at a desired (constant) level, a substitution infusion fluid is added to the blood stream in the extracorporeal circuit, after is has passed through the artificial kidney and before it re-enters the patient's vein.

In a normal CVVH procedure, approximately 50 liters of filtrate are removed per 24 hours, and approximately the same amount of substitution infusion fluid is added into the return of blood side of the extracorporeal circuit. The substitution infusion fluid commonly used is conventional infusion fluid comprising a physiological saline solution generally only containing about 140 mmol/L of sodium ions, 1.6 mmol/L of calcium ions, 0.75 mmol/L of magnesium ions, 36 mmol/L of bicarbonate ions, and 110 mmol/L of chloride ions. All forms of hemodialysis or hemodiafiltration therapies are characteristically different from pure hemofiltration by the use of a dialysate fluid flow along the semipermeable membrane side opposite to the blood side.

In order to prevent coagulation of the blood during hemofiltration, usually an anticoagulant is added to the blood in the extracorporeal circuit before it enters the artificial kidney. In the past, heparin or fractionated heparin was often used for this purpose. A drawback of the use of heparin, however, is that this use leads to systemic anticoagulation (i.e., anticoagulation of all blood including that within the patient), giving rise to the risk of the occurrence of serious bleeding complications, particularly in seriously ill patients.

Instead of heparin, citrate ions can be used as an anticoagulant for hemodialysis. Citrate ions, usually added in the form of trisodium citrate, are believed to bind free calcium ions in the blood, which have a pivotal role in the coagulation cascade. Citrate ions, added to the blood into the extracorporeal circuit before it enters the artificial kidney, are only active as an anticoagulant in the extracorporeal circuit, whereby the risk of bleeding complications due to systemic anticoagulation is avoided. When citrate ions are applied during hemodialysis forms of treatment, a calcium-and-magnesium-free substitution fluid or dialysate is required. Therefore, the application of citrate ions during hemodialysis is more complex than during pure hemofiltration.

Citrate ions are mainly metabolized in skeletal muscle and liver tissue. Only in cases of severe hepatic failure combined with severe shock, or of certain (rare) metabolic diseases, the metabolism of citrate may run short, leading to too high citrate concentrations in the systemic blood circulation, which on its turn may endanger the patient. Accordingly, citrate ions are an attractive anticoagulant for use in pure hemofiltration procedures, especially for use in CVVH treatment in ICU patients.

Because citrate ions bind to positively charged metal ions like calcium, magnesium, iron, zinc, copper, and manganese, these ions are partly removed in the artificial kidney, leading to a net removal of calcium and magnesium ions and other metal ions from the patient's blood. As a result, hypocalcemia and/or hypomagnesemia and/or shortages of other metal ions may be induced in the patient that can lead to life-threatening complications. The process of hemofiltration, also induces a net removal of phosphate and potassium ions, trace elements, water-soluble vitamins, amino acids and of glucose in the artificial kidney. This may lead to significant degrees of hypovolemia, hypophosphatemia, hypokalemia, with a risk of deteriorating the patient's condition. Hypophosphatemia may also induce life-threatening complications in the patient.

Therefore, there is a need in the art for an extracorporeal blood treatment system that is capable of introducing an appropriate volume of substitution infusion fluid per unit of time and an appropriate volume of anticoagulation solution per unit of time to prevent complications from occurring to the patient.

SUMMARY OF THE INVENTION

One embodiment of the invention provides a hemofiltration system having an access line configured to carry blood from a patient's blood stream, a first pump configured to pump the blood through the access line, a second pump for introducing an anticoagulant solution into the blood traveling through the access line, a filter for filtering the blood traveling through the access line, a third pump for introducing a substitution fluid into the blood, a fourth pump for introducing a calcium and magnesium solution into the blood, a return line configured to carry blood back to the patient's blood stream, and a processing unit for controlling a flow rate for the first pump, the second pump, the third pump, and the fourth pump, the fourth pump being coupled to the return line. The third pump may be coupled to the access line or the return line.

Another embodiment of the invention provides a hemofiltration method for pumping blood from a patient's blood stream into an access line, introducing an anticoagulant solution into the pumped blood, filtering the pumped blood, delivering the pumped blood from the filtering step to a return line, introducing a substitution fluid into the pumped blood, introducing a calcium and magnesium solution into the blood traveling through the return line, and returning the blood back to the patient's blood stream. The substitution fluid may be introduced to the access line or the return line.

DETAILED DESCRIPTION

Methods and systems that implement the embodiments of the various features of the invention will now be described with reference to the drawings. The drawings and the associated descriptions are provided to illustrate embodiments of the invention and not to limit the scope of the invention. Reference in the specification to "one embodiment" or "an embodiment" is intended to indicate that a particular feature, structure, or characteristic described in connection with the embodiment is included in at least an embodiment of the invention. The appearances of the phrase "in one embodiment" or "an embodiment" in various places in the specification are not necessarily all referring to the same embodiment. Throughout the drawings, reference numbers are re-used to indicate correspondence between referenced elements.

FIGS. 1-4 illustrate various embodiments of the invention for an extracorporeal blood treatment system. In this system, blood is extracted from a vein of a patient and transported to an artificial kidney 60 via the access line 1 of an extracorporeal circuit by the driving force of a blood pump 14. In one embodiment, a pressure monitoring system, shown in FIGS. 4 as 19 and 21, is connected to the access line 1 pre- and post-blood pump 14 to control the depressurization created by the pumping system of blood from the patient and pressurization created by the pump 14 before the artificial kidney 60. The connections or inlet ports (not shown) for the pressure monitoring system 19 and 21 may include a closing system, such as a valve, a mechanical clamp, or a male Luer-lock connector.

Figure 1:
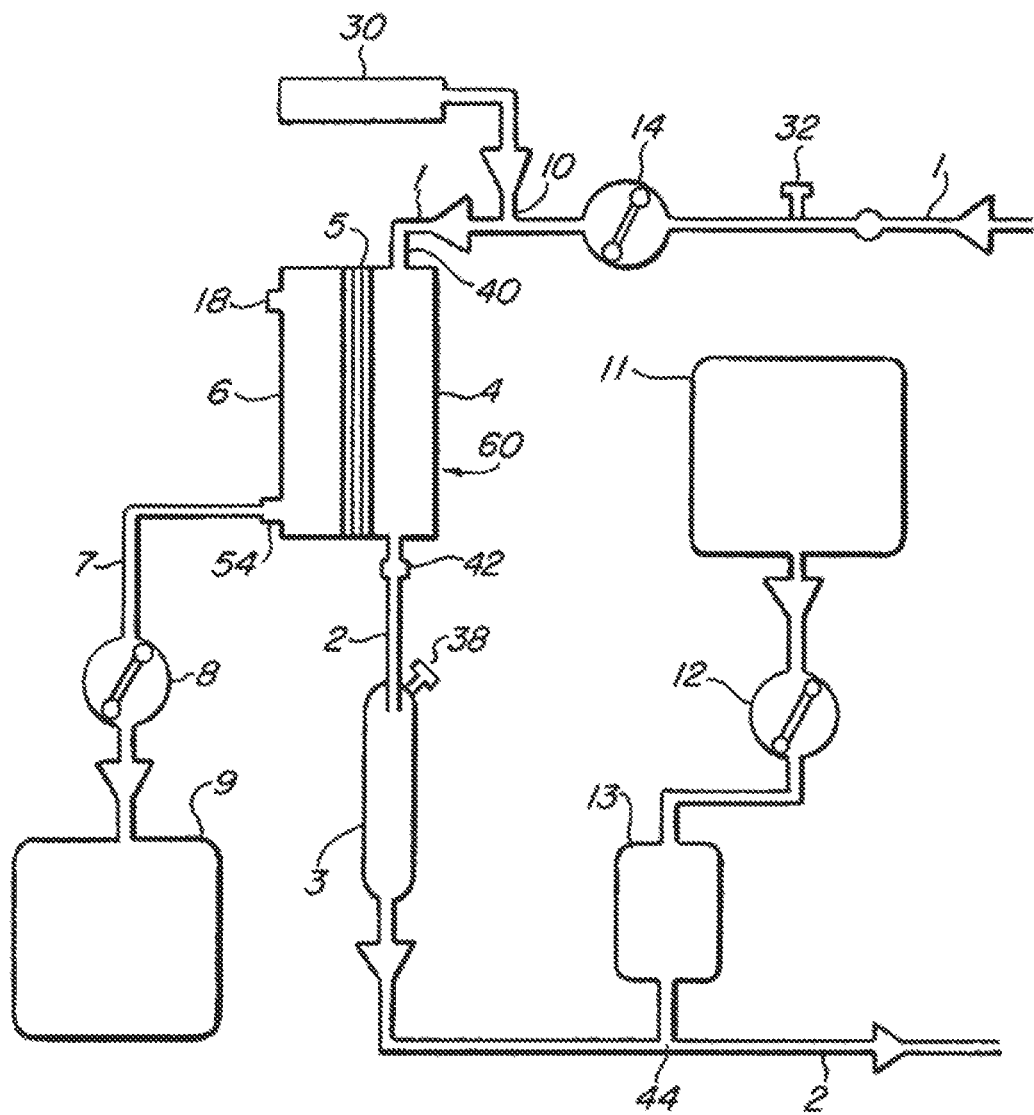
FIG. 1 illustrates an extracorporeal blood treatment system according to one embodiment of the invention.
Figure 4:
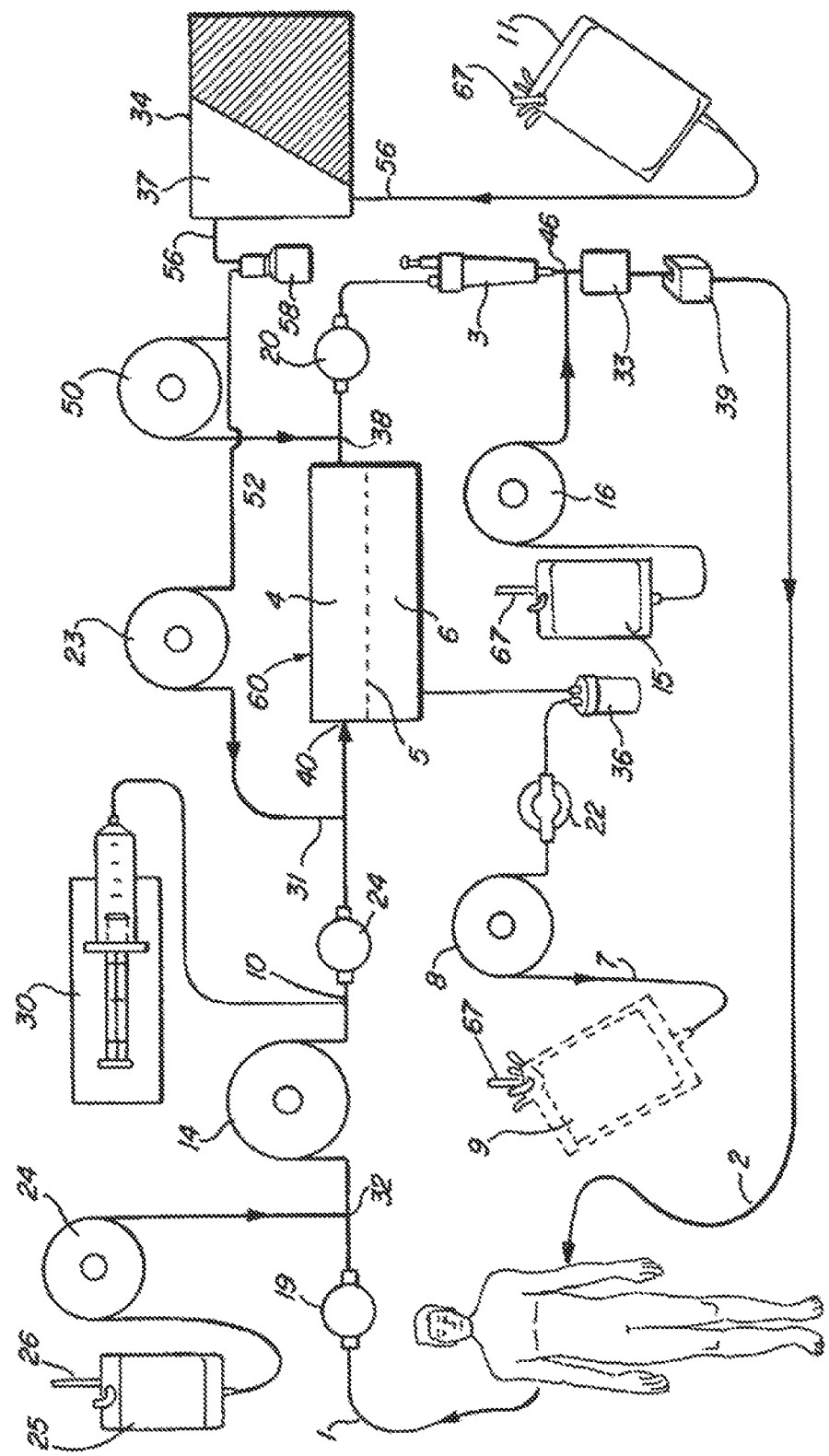
FIG. 4 illustrates an extracorporeal blood treatment system that infuses an anticoagulant before and after the blood pump on the access line and introduces a substitution infusion fluid to the access line in conjunction with the return line according to one embodiment of the invention.

An anticoagulant solution, such as a citrate or heparin anticoagulation solution, can be infused from a reservoir, shown in FIG. 4 as 25 or 30, to the access line 1 of the extra-corporeal circuit. In One embodiment, the anticoagulant solution can be pumped 24 to the access line 1 pre-blood pump 14 at inlet port 32. As shown in FIG. 1, the anticoagulant solution can also be infused to the access line 1 post-blood pump 14 at inlet port 10. Both inlet ports 10 and 32 may contain a closing system, such as a valve, a mechanical clamp, or Luer-lock connectors. In one embodiment, the anticoagulant solution passes through a drip chamber or air trap (device not shown) before being infused into the access line 1 of the extra-corporal circuit. The anticoagulant line can be color coded black.

By using the citrate anticoagulation infusion fluid in an extracorporeal blood treatment system, the blood is effectively anticoagulated within the extracorporeal circuit and not within the systemic circulation of the patient and the concentrations of sodium, potassium, calcium, magnesium, and bicarbonate ions remain substantially within ranges of which it is accepted that they do not lead to unacceptable risk of complications within the patient. This citrate anticoagulant solution could be used in any appropriate extracorporeal blood treatment and is especially useful during all kinds of pure hemofiltration procedures in combination with the matching substitution infusion fluids according to the invention.

In one exemplary embodiment, the citrate anticoagulation solution for pure hemofiltration treatment can be an aqueous solution comprising about 38 mmol/L of citric acid and about 212 mmol/L of trisodium citrate. This citrate anticoagulation solution can be used during pure CVVH in combination with a matching substitution infusion fluid comprising about 118 mmol/L of sodium ions, about 2.3 mmol/L of calcium ions, about 2.6 mmol/L of potassium ions, about 0.8 mmol/L of phosphate ions, about 0.9 mmol/L of magnesium ions, about 6.5 mmol/L of glucose, less than about 5.5 mmol/L of acetic acid, and chloride ions to keep electrochemical balance. Moreover, it may be desirable to add about 0.0 mmol/L to about 5.5 mmol/L of acetate ions to prevent the formation of calcium phosphate sedimentation in the one part substitution infusion fluid. In other embodiments, for example, glucose and/or acetic acid and/or phosphate may be omitted, as well as concentrations of other ingredients can be adjusted up or down as necessary.

The mixture of blood with anticoagulation solution travels down the access line of the extra-corporeal circuit. At the end of the access line 1 are one or more connectors 40, such as male and female ISO connectors, that couple the access line 1 to the artificial kidney 60. In the artificial kidney 60, the blood can be filtered through a semi-permeable membrane 5. Fluids contained in the blood and/or introduced from inlet dialysate port 18 are drained from the filtrate compartment 6 of the artificial kidney 60 via connecting tubing 7 to a collection reservoir 9. The tubing 7 is coupled to the artificial kidney 60 using one or more connectors 54, such as male and female Luer-Lock connectors. A pump 8 moves the filtrate into the collection reservoir 9 and generates an effluent flow rate.

As shown in FIG. 4, the connecting tubing 7 may be coupled to a pressure monitoring system 22 for controlling filtrate pressurization. Also, the connecting tubing 7 is connected to a blood leak detector chamber 36 for controlling leakage of red blood cells through the membrane 5 of the artificial kidney 60. In one embodiment, the connecting tubing 7 may include a closing system, such as a mechanical clamp, between the pump 8 and the collection reservoir 9. The connecting tubing 7 may be connected to the collection reservoir 9 using connectors, such as male and female Luer-lock connectors.

A retentate blood is transported back from a retentate compartment 4 of the artificial kidney 60 to the patient's blood stream via the return line 2 of the extracorporeal circuit, after passage through an air trap 3. The artificial kidney 60 is coupled to the return line 2 using one or more connectors 42, such as male and female ISO connectors. The air trap 3 serves to remove all air bubbles from the blood before it is returned into the patient's blood stream. Preferably, the blood is returned into the patient's blood stream at the same place as at which it was extracted, e.g., by way of a double-lumen venous catheter. In one embodiment, the access line 1 may be color coded red, the return line 2 may be color coded blue, and the filtrate connecting tubing 7 may be color coded yellow.

Before the hemofiltered blood is returned to the patient, a substitution infusion fluid can be infused to the return line 2 of the extra-corporeal circuit. In one embodiment, a one-part substitution fluid, stored in reservoir 11 of FIG. 1, may be an aqueous fluid for extra-corporeal treatments comprising (as used herein mmol/L is "millimoles" of the salt or ion per liter of aqueous substitution infusion fluid) between 0.2 and 1, preferably between 0.5 and 0.9 mmol/L of dihydrogen phosphate ions; between 70 and 130, preferably between 90 and 120 mmol/L of sodium ions; between 1.6 and 2.6, preferably between 1.9 and 2.4 mmol/L of calcium ions; between 0.25 and 1.25, preferably between 0.5 and 1.0 mmol/L of magnesium ions; between 1 and 4, preferably between 1.8 and 3.5 mmol/L of potassium ions; between 2 and 11.5, preferably between 5.5 and 7.5 mmol/L of glucose; below 5.5 mmol/L, preferably between 0 and 3.1 mmol/L of acetate ions; and below 5.5. mmol/L, preferably between 0 and 3.1 mmol/L of bicarbonate ions. This substitution infusion fluid is usually supplemented with chloride ions to achieve a neutral electrochemical balance.

In another embodiment, the one-part substitution infusion fluid may be an aqueous solution, preferably comprising about 117 mmol/L of sodium ions, about 2.5 mmol/L of potassium ions, about 0.83 mmol/L of phosphate ions, about 2.3 mmol/L of calcium ions, about 0.89 mmol/L of magnesium ions, about 6.4 mmol/L of glucose, and less than about 3.1 mmol/L of acetate ions, in the absence of bicarbonate ions, and supplemented with chloride ions to keep electrochemical balance.

Figure 2:
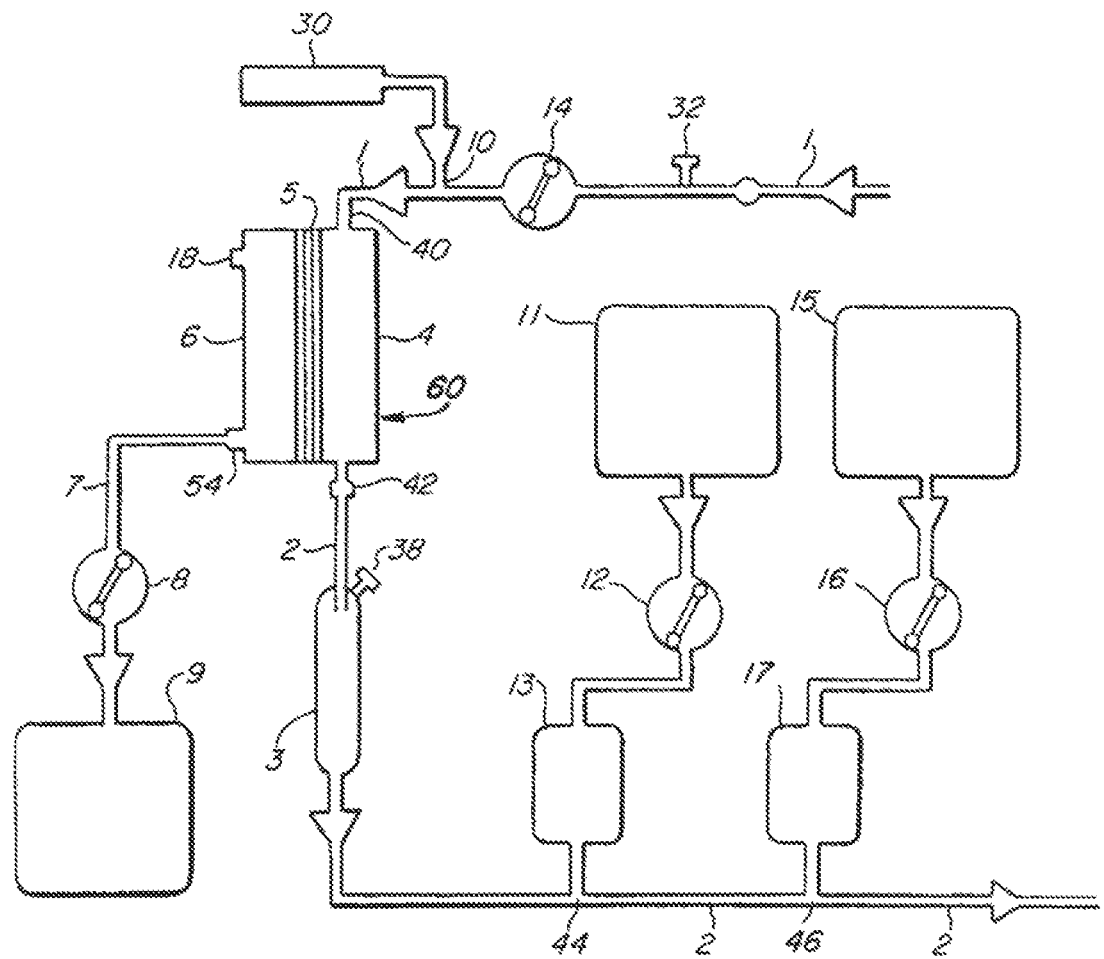
FIG. 2 illustrates an extracorporeal blood treatment system according to one embodiment of the invention.

As shown in FIG. 2, the substitution infusion fluid may be infused to the return line 2 of the extra-corporeal circuit, post-bubble air trap 3, at connection 44. Another substitution solution may be infused to the return line 2 of the extra-corporeal circuit, post-bubble air trap 3, at connection 46. A two-part aqueous substitution infusion fluid made in accordance with the teachings of the invention may include a first aqueous substitution infusion fluid comprising from about 70 mmol/L to about 130 mmol/L of sodium ion, from about 0.01 mmol/L to about 5 mmol/L of potassium ion, from about 100 mmol/L to about 150 mmol/L of chloride ion, from about 0.01 mmol/L to about 1.5 mmol/L of phosphate ion and, optionally, from about 2 mmol/L to about 11.5 mmol/L of glucose.

The first substitution infusion fluid described above could then be used in combination with a second aqueous infusion fluid comprising from about 10 mmol/L to about 35 mmol/L of calcium ion, from about 2.5 mmol/L to about 20 mmol/L of magnesium ion and, optionally, from about 30 mmol/L to about 100 mmol/L of any one or more of sulphate, gluconate, glubionate or chloride ion.

Both the one-part and the two-part substitution infusion fluids may be used with a matching citrate solution. The same citrate solution may be used regardless of whether a one part or two-part substitution infusion fluid is used. Thus by using the specific substitution infusion fluid together with a matching citrate anticoagulant solution in an extracorporeal blood treatment procedure, the concentrations of potassium, phosphate, calcium, magnesium, bicarbonate ions, and glucose remain substantially within acceptable ranges. In most cases, the concentrations of these ions and glucose remain more or less constant in the systemic blood of the patient undergoing, for example, hemofiltration. Consequently, the chances of the occurrence of the problems encountered in hemofiltration to date are significantly reduced, if not eliminated altogether. Particularly, the chances of the above-indicated complications including electrolyte or acid-base abnormalities and/or severe bleeding are significantly reduced.

The substitution infusion fluids, according to the invention, may be conveniently prepared by dissolving salts in water in such amounts that the desired concentrations are reached, as is well within the expertise of the normal person skilled in the art. During preparation, it. is desired that a sterile environment is maintained. Accordingly, the substitution infusion fluids preferably are sterile, according to the European Pharmacopeia or United States (US) Pharmacopeia, thereby avoiding the risk of infections in a patient when the fluids are used during hemofiltration.

Typically, substitution infusion fluids are hypotonic. Exemplary values are between 200 and 270 mOsm/L. Nevertheless, it has been found that the fluid is well tolerated by patients when it is used in a hemofiltration procedure. It has been found that the hypotonicity is in fact beneficial by compensating for the hypertonicity induced at the arterial side of the extracorporeal circuit by the anticoagulant. The result is that the blood that is returned into the patient's blood stream has substantially normal (physiological) osmolarity.

It has been found that when a two-part substitution infusion fluid of this type is used in combination with a matching solution of trisodium citrate comprising, for example, of about 106-300 mmol/L trisodium citrate as an anticoagulant, the concentrations of the indicated ions in the patient's blood remain substantially within the physiological range throughout the pure hemofiltration procedure.

In one preferred embodiment, the present citrate anticoagulation solution, for example, for pure hemofiltration treatment is an aqueous solution meeting the above requirements, comprising about 38-39 mmol/L of citric acid and about 211-212 mmol/L of trisodium citrate. This citrate anticoagulation solution is preferably used in combination with a matching two part substitution infusion fluid as disclosed above.

By using the citrate anticoagulation infusion fluid according to the invention in an extracorporeal treatment, the blood is effectively anticoagulated within the extracorporeal circuit and not within the systemic circulation of the patient and the concentrations of sodium, potassium, calcium, magnesium, and bicarbonate ions remain substantially within ranges of which it is accepted that they do not lead to unacceptable risk of complications within the patient. This citrate anticoagulant solution can be used in any appropriate extracorporeal blood treatment and is especially useful during all kinds of pure hemofiltration procedures in combination with the matching substitution infusion fluids according to the invention.

In another embodiment of the invention, the two-part substitution infusion fluid is used in combination with the matching citrate solution. Such two-part substitution infusion fluid for use in various extracorporeal treatments will comprise a first infusion substitution fluid including electrolytes, but excluding calcium and magnesium, and a second infusion fluid comprising calcium and magnesium. In one preferred example, the two part substitution infusion fluid may comprise a first substitution infusion fluid comprising between about 117 and about 129 mmol/L of sodium, between about 2.5 and about 3.0 mmol/L of potassium, between about 115 and about 140 mmol/L of chloride and between about 0.7 and about 0.9 mmol/L of phosphate; and a second substitution infusion fluid may comprise between about 15 and about 25 mmol/L of calcium and between about 10 and about 12 mmol/L of magnesium ions. Optionally, the first substitution infusion fluid may also comprise between about 6.5 and about 7.1 mmol/L of glucose. In other embodiments, between 0.4 and 0.8 mmol/L of phosphate ions may be added to either the first of the second solution.

In one embodiment, calcium ion provided in the form of a calcium salt selected from the group comprising calcium glubionate, calcium chloride and calcium gluconate and magnesium ion is provided in the form of a magnesium salt selected from the group comprising magnesium sulfate, magnesium chloride, magnesium glubionate and magnesium gluconate.

In yet another preferred embodiment the two-part substitution infusion fluid comprises a first substitution infusion fluid comprising about 117 to about 118 mmol/L of sodium, about 6.5 to about 6.8 mmol/L of glucose, about 2.6 to about 2.8 mmol/L of potassium, about 115 mmol/L to about 140 mmol/L of chloride and about 0.8 mmol/L phosphate; and a second substitution infusion fluid comprising about 15 to about 24 mmol/L of calcium and from about 10 to about 15.5 mmol/L of magnesium ions. In a further preferred embodiment, the first substitution infusion fluid may comprise about 118-119 mmol/L of chloride ion. In yet another preferred embodiment, the second infusion fluid may comprise about 24 mmol/L of calcium and about 10.8 mmol/L of magnesium.

As shown in FIG. 4, the substitution infusion fluid may be infused to the return line 2 of the extra-corporeal circuit, pre-bubble air trap 3, at connection 38 (if the calcium ions and the magnesium ions are not present in the substitution infusion fluid) or post-bubble air trap 3 at connection 44 but before air detection system 33. In CVVH, the substitution infusion fluid may also be infused to the access line 1 of the extra-corporeal circuit, post-blood pump 14, at inlet port 10 or pre-blood pump 14 at inlet port 32. For CVVHD and CVVHDF, the substitution infusion fluid may be pumped to the inlet dialysate port 18 of the artificial kidney 60 via a dialysate line (not shown). The dialysate line can be pre-connected or removeably engageable with the artificial kidney 60 using couplers, such as male and female Luer-lock connectors. The dialysate line may be color coded purple.

The substitution infusion fluid (without the calcium ions and the magnesium ions) for CVVHDF can also be infused to the return line 2 of the extra-corporeal circuit pre-bubble air trap 3 at connection 38 or post-bubble air trap 3 at connection 44 but before an air detection system 33. It is understood to a person skilled in the art that the substitution infusion fluid can be infused to the access line in conjunction with the return line. Some of the embodiments utilize a substitution infusion fluid that does not contain calcium and magnesium ions.

The substitution infusion fluid can be added from the reservoir 11, via a pump 12 and a heater 13. The heater 13 ensures that the substitution infusion fluid ultimately entering the patient's body is substantially equal to the patient's body temperature, thus making the entire procedure substantially less uncomfortable. In one embodiment, a pressure monitoring system, shown in FIG. 4 as 20, is connected to the return line 2 to control pressurization of tubing segment containing blood re-infused to the patient. In addition, an air detection system 33 can be used on the return line 2 to detect any air bubbles that may have been introduced with the substitution infusion fluid.

FIG. 2 depicts an embodiment wherein the two-part substitution infusion is provided with two reservoirs 11 and 15 that supply the first substitution infusion fluid and the second substitution infusion fluid, respectively, via separate pumps 12 and 16 and heaters 13 and 17. If the volume of the calcium/magnesium substitution infusion fluid is relatively small, then it may not be necessary to heat such substitution infusion fluid and, therefore, the second heater 17 may be optional. The flow or volume of the supplied substitution infusion fluid may be controlled by connectors 44 and 46. Connectors 44 and 46 may have a closing system, such as a valve, a mechanical clamp, or Luer-lock connectors. These connectors 44 and 46 are preferably coupled to the return line 2 prior to the connection of the air detection system (device not shown in FIG. 2). The second substitution infusion fluid line can be color coded white.

In one embodiment, the substitution infusion fluid or a mixture containing the retentate blood with the substitution infusion fluid, passes through a drip chamber or air detection system, shown in FIG. 4 as 33, before flowing back to the patient via the return line 2. An automatic return line clamp 39 is preferably used post air detection system 33 in order to automatically close return line 2 in case of air detection or return line 2 disconnection from catheter return way detected by a low return pressure value.

During the procedure, the amount of filtrate collected in the collection reservoir 9 is determined accurately, e.g., by weighing. The amount of substitution infusion fluid added to the blood is adapted to this amount. This makes it possible to make sure that an exactly predetermined volume of fluid is returned to the patient's body, matching the originally extracted volume therefrom or adapted to the fluid balance needed in a particular patient. The flow through pumps 8 and 12, or 8 and 16, or 8, 12 and 16, are accordingly precisely adjusted to one another. Typically, the substitution infusion fluid is administered (infused) into the blood at a rate of between about 1 and 80 ml/min per 200 ml/min blood. In practice, alerting means, such as an audible alarm, are often provided for alerting nursing personnel should an interruption of the blood, filtrate, or substitution flow occur. Typically, said specific anticoagulation fluid of trisodium citrate and citric acid is infused into the blood at a rate of between about 1.3 and 4 ml/min per 200 ml/min blood.

Figure 3:
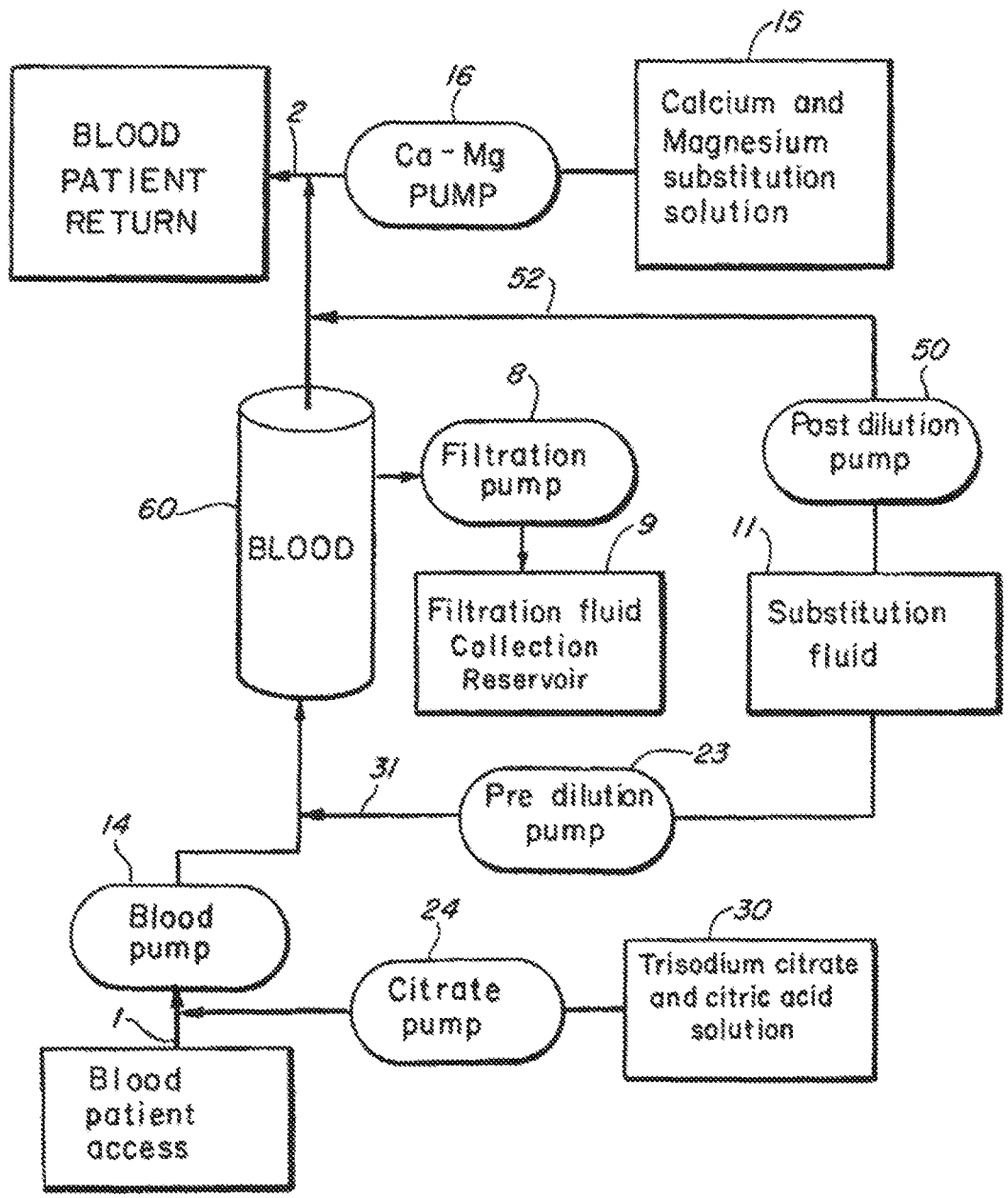
FIG. 3 illustrates an extracorporeal blood treatment system that introduces a substitution infusion fluid to the access line in conjunction with the return line according to one embodiment of the invention.

FIG. 3 illustrates another hemofiltration process according to one embodiment of the invention. In this embodiment, the substitution infusion fluid can be introduced to the access line 1 of the extra-corporeal circuit via a pre-dilution line 31 and to the return line 2 of the extra-corporeal circuit via a post-dilution line 52. A pre-dilution pump 23, also shown in FIG. 4, pumps the first substitution infusion fluid from the reservoir 11 to the pre-dilution line 31. Furthermore, a post-dilution pump 50, also referred to herein as first post-dilution pump 50, pumps the first substitution infusion fluid from the reservoir 11 to the post-dilution line 52. In this embodiment, the substitution infusion fluid does not include calcium and magnesium ions.

FIG. 4 shows a heating system 34 coupled to the dilation lines 31 and 52. The heating system 34 preferably contains a chamber 37 where gas can be removed from fluid before infusing to the extra-corporal circuit and where temperature of fluid is controlled. This degassing chamber 37 contains first and second infusion ports with a closing system, such as a valve, a mechanical clamp or Luer-lock connectors. The closing system is preferably used before the heating system 34.

In one embodiment, a pumping system (device not shown) is used to remove gas from the degassing chamber 37 during priming and treatment. The heating system 34 may also be coupled to a temperature sensor 58 in order to regulate and control the temperature of the heated fluid. In addition, a serial tubing 56 can be used to send substitution infusion fluids to post-dilution line 52, pre-dilution line 31 and/or dialysate line (not shown).

FIGS. 3 and 4 show the pre-dilution line 31 connected to the access line 1 post-blood pump 14. In one embodiment, the pre-dilution line 31 is connected to the access line 1 pre-blood pump 14. The pre-dilution line 31 can be pre-connected or removeably engageable with couplers on access line 1. FIG. 4 also shows the post-dilution line 52 can be connected to the return line 2 pre-air trap 3. In one embodiment, the post-dilution line 52 is connected to the return line 2 post-air trap 3. Likewise, the post-dilution line 52 can be pre-connected or removeably engageable with couplers on return line 2. In addition, the pre-dilution line 31 and post-dilution line 52 may have one or more connectors, such as Luer-lock connectors, to couple one or more reservoirs 11 of the substitution infusion fluid. Pre-dilution line 31 and post-dilution line 52 may be color coded green.

Figure 5:
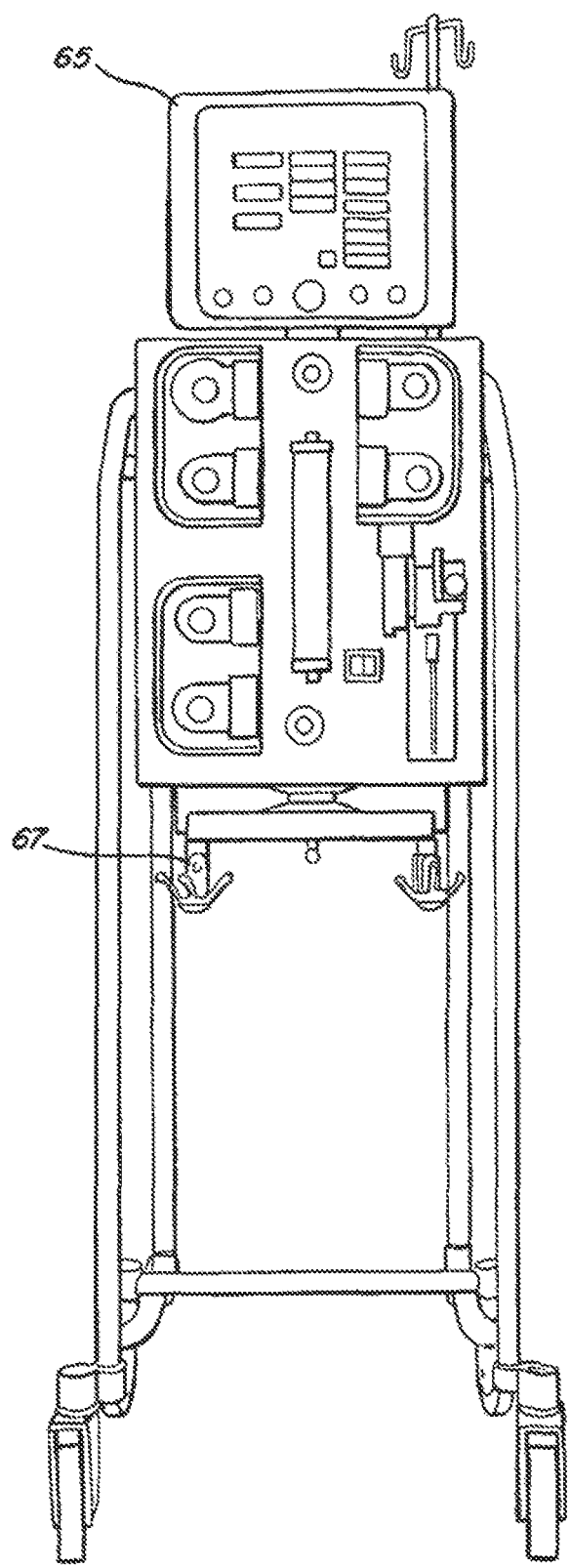
FIG. 5 illustrates an extracorporeal blood treatment system with a monitor system according to one embodiment of the invention.

FIG. 5 illustrates an extracorporeal blood treatment system with a monitoring system 65, according to one embodiment of the invention. The monitoring system 65 can have sensor indicators to notify the user on the status of the extracorporeal blood treatment system. The monitoring system 65 can also facilitate control of the extracorporeal blood treatment system, including but not limited to, a blood pump 14, a filtrate pump 8, a first post-dilution pump 50, a pre-dilution pump 23, a dialysate pump (device not shown), an anticoagulant pump 24, a second post-dilution pump 16, and a scale system 67. The monitoring system 65 can provide a user friendly interface to allow for therapies, such as but not limited to, CVVH, CVVHD, and CVVHDF. The monitoring system 65 can also provide control of the heating system 34, blood leakage detector 36, and air bubble detector 33. Furthermore, the monitoring system 65 can also have indicators for pressure sensors 19, 20, 21 and 22.

The pumps utilized in the extracorporeal blood treatment system are those typically used in the industry, such as pulsed motor pumps and step motor pumps. The pulsed increase or the number of steps for one unit of blood flow rate (1 ml/min) increase can be defined during a calibration process. The blood pump 14 preferably maintains a blood flow rate between about 10 ml/min ("MinBFR") and about 500 ml/min ("MaxBFR"). The filtrate pump 8 preferably maintains a filtrate flow less than about 14,000 ml/h. The pre-dilution pump 23, the post-dilution pump 50, and the dialysate pump (device not shown), preferably maintain a flow rate less than about 10,000 ml/h. The anticoagulant pump 24 and the second post-dilution pump preferably maintain a flow rate less than about 1000 ml/h. The solution compositions and the flow rates described herein are examples are not intended to limit the scope of the invention.

In one embodiment, if the pre-dilution, post-dilution and dialysate solutions are the same solution and connected to the same substitution tubing 56, then their respective pumps 50, 23 and 24 can be regulated and controlled together.

Since the infusion of all fluids are regulated and controlled together, when the blood pump 14 is running, all other pumps must be activated. However, when one of the pumps halts for any reason, the other pumps may also stop pumping. Unfortunately, when the blood pump 14 stops, there is a risk of blood clotting inside the return line 2. Since the access line 1 of the extra-corporal circuit has citrate in it, the risk of clotting inside this part is low. Therefore, when one pump halts for any reason, the stops of blood pump 14 and anticoagulant pump 24 are preferably delayed by, for example, about 10 seconds after the other pumps have already stopped. This allows the return line 2 and return catheter way to fill with blood containing citrate and avoid clotting during the halting of the blood pump 14. This may require an algorithm referred to herein as "Stop Blood Pump Program."

A scale system 67 may be configured to accept the handling of more than one reservoir; preferably four reservoirs 25, 9, 11, and 15. If the scale 67 is configured to handle these reservoirs, then the maximum overloaded weight will be greater than about 24 kg. In one embodiment, the scale system 67 is configured to handle more than one reservoir 25, more than one reservoir 9, more than one reservoir 11, and more than one reservoir 15. The scale system 67 preferably has a gauge constraint unit (device not shown) to aid in controlling and regulating the pumps' flow rate.

Figure 6:
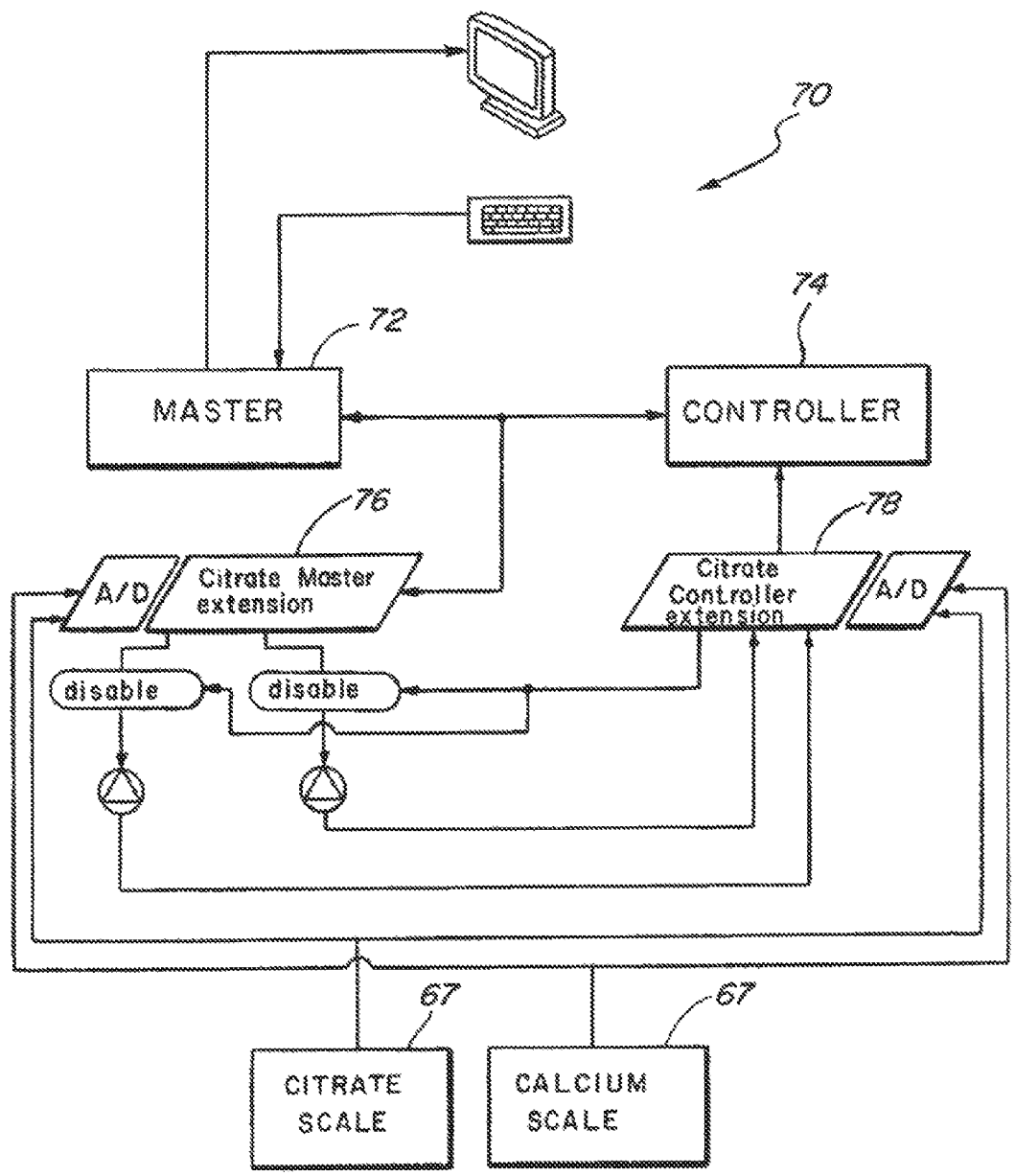
FIG. 6 illustrates a simplified block diagram of a control system that regulates, controls, and monitors the operations of the extracorporeal blood treatment system according to one embodiment of the invention.

FIG. 6 illustrates a simplified block diagram of a control system 70 that regulates, controls, and monitors the operations of the extracorporeal blood treatment system. The control system 70 may include one or more processing units (e.g., a master processing unit 72 and a controller 74). The control system 70 may also include a master extension 76 and a controller extension 78. The master extension 76 monitors the feedback data (pump and scale data) for the master processing unit 72 and dictates the flow rate of the citrate and calcium pumps depending on the scale data (citrate and calcium scale)

and the programming values from the master processing unit 72. The controller extension 78 retrieves the encoder data from the citrate and calcium pumps and monitors the adequate flow rate. In the case of a deviation between the received value and the set parameters, the controller extension 78 is able to stop the citrate and calcium pumps. This data from the protective subsystem are sent to the controller 74. Moreover, the controller extension 78 receives data from the controller 74.

All controls and monitoring are performed electronically using computer algorithms. When programming a treatment, filtrate flow rate is linked to programming values for post-dilution flow rate, pre-dilution flow rate, dialysate flow rate, anticoagulant flow rate, second substitution infusion fluid flow rate, and fluid loss rate. The relationship between the flow rates is: the filtrate flow rate equals the sum of post-dilution flow rate, pre-dilution flow rate, dialysate flow rate, anticoagulant flow rate, second substitution solution flow rate, and fluid loss rate.

When the citrate anticoagulant solution is added to the blood, calcium ions are fixed by citrate molecules or metabolized by a patient's liver and muscles such that calcium ions are released to the blood and citrate molecules are converted into bicarbonate molecules. The kinetics for liver and muscles metabolism take time to be efficient, and therefore, to avoid Calcium/citrate molecules accumulation or metabolic acidosis during first minutes of treatment, another algorithm can be used in order to increase progressively working flow rates to the programming flow rates during the first minutes of treatment.

This algorithm used in increasing progressively working flow rates utilizes a Ratio (R) that depends on programming blood flow rate, and a frequency value (1/T). Blood flow rate starts with MinBFR and is increased each time T interval from a fixed value (1 per 1 ml/min or 10 per 10 ml/min). Ratio R is calculated by dividing the working blood flow rate by the programming blood flow rate. At each time T interval, all working flow rates (post-dilution, pre-dilution, dialysate, filtrate, anticoagulant, and second substitution infusion fluid flow rates) are modified such that the working flow rate equals Ratio R multiplied by programming flow rate. This time T for progressive increase of working flow rates is referred to as "Regulated Start Mode." The Regulated Start Mode is automatically achieved once the working blood flow rate reaches the programming flow rate value.

When pre-dilution substitution infusion fluid is infused pre-blood pump 14 and/or anticoagulant (citrate) solution is infused pre-blood pump 14, the real working blood flow rate is equal to the sum of programming blood flow rate, pre-dilution flow rate, and anticoagulant (citrate) flow rate.

When citrate molecules for anticoagulant are included into a substitution infusion fluid used as pre-dilution solution, the anticoagulant (citrate) flow rate can be programmed to 0 ml/h. When calcium and magnesium ions are included into a substitution infusion fluid used as post-dilution solution, the second solution containing calcium and magnesium ions may not be necessary, and therefore, the flow rate of the second substitution infusion fluid can be programmed to 0 ml/h.

In one embodiment, the extracorporeal blood treatment system may include a heparin pump system (device not shown) in order to keep the possibility of using heparin as anticoagulant when patient metabolism cannot allow the citrate anticoagulant process. When a patient's metabolism cannot allow use of a citrate anticoagulant process, anticoagulant (citrate) flow rate can be programmed to 0 ml/h and the second substitution infusion fluid (Calcium/Magnesium solution) flow rate can be programmed to 0 ml/h.

In another embodiment, the extracorporeal blood treatment system may contain an algorithm to control the Trans-Membrane Pressure (TMP) as a mathematical relation between return pressure 20, pre-filter pressure 21 and filtrate pressure 22. According to this relationship, TMP is equal to the sum of return pressure 20 with pre-filter pressure 21 divided by 2 and subtracted by the filtrate pressure 22. The extra-corporal blood treatment system also contains an algorithm to control the Pressure Drop (PD) through blood compartment 4 of the artificial kidney 60 as a mathematical relation between return pressure 20 and pre-filter pressure 21. According to this relationship, PD is equal to the pre-filter pressure 21 minus return pressure 20 plus a Correcting Factor (CF), where CF is evaluated by the difference of positioning level between the return pressure sensor 20 and the pressure sensor 21.

Those skilled in the art will appreciate that the various illustrative logical components, blocks, modules, circuits, and algorithms described in connection with the embodiments disclosed herein may be implemented as electronic hardware, computer software, or combinations of both. To illustrate this interchangeability of hardware and software, various illustrative components, blocks, modules, circuits, and algorithms have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processing device, a digital signal processing device (DSP), an application specific integrated circuit (ASIC), a field programmable gate array (FPGA) or other programmable logic device, discrete gate or transistor logic, discrete hardware components, or any combination thereof designed to perform the functions described herein. A general purpose processing device may be a microprocessing device, but in the alternative, the processing device may be any conventional processing device, processing device, microprocessing device, or state machine. A processing device may also be implemented as a combination of computing devices, e.g., a combination of a DSP and a microprocessing device, a plurality of microprocessing devices, one or more microprocessing devices in conjunction with a DSP core or any other such configuration.

The methods or algorithms described in connection with the embodiments disclosed herein may be embodied directly in hardware, software, or combination thereof. In software the methods or algorithms may be embodied in one or more instructions that may be executed by a processing device. The instructions may reside in RAM memory, flash memory, ROM memory, EPROM memory, EEPROM memory, registers, hard disk, a removable disk, a CD-ROM, or any other form of storage medium known in the art. An exemplary storage medium is coupled to the processing device such the processing device can read information from, and write information to, the storage medium. In the alternative, the storage medium may be integral to the processing device. The processing device and the storage medium may reside in an ASIC. The ASIC may reside in a user terminal. In the alternative, the processing device and the storage medium may reside as discrete components in a user terminal.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described preferred embodiment can be configured without departing from the scope and spirit of the invention. Therefore, it is to be understood that, within the scope of the appended claims, the invention may be practiced other than as specifically described herein.

The invention claimed is:

1. A machine-readable medium embodying instructions that may be performed by one or more processors, the instructions comprising:
   instructions for pumping blood from a patient's blood stream into an access line;
   instructions for introducing an anticoagulant solution into the pumped blood;
   instructions for filtering the pumped blood;
   instructions for delivering the pumped blood from the filtering step to a return line;
   instructions for introducing a substitution fluid into the pumped blood;
   instructions for introducing a calcium and magnesium solution into the blood traveling through the return line; and
   instructions for returning the blood back to the patient's blood stream.

2. The machine-readable medium of claim 1, wherein the substitution fluid is introduced into the access line.

3. The machine-readable medium of claim 1, wherein the substitution fluid is introduced into the return line.

4. The machine-readable medium of claim 1, wherein the substitution fluid is introduced into the access line and into the return line.

5. The machine-readable medium of claim 1, further comprising instructions for monitoring the blood pressure in the access line.

6. The machine-readable medium of claim 1, further comprising instructions for monitoring the blood pressure in the return line.

7. The machine-readable medium of claim 1, further comprising:
   instructions for exporting through a filtrate line a filtrate obtained from the filtering step; and
   instructions for monitoring the pressure in the filtrate line to control filtrate pressurization.

8. The machine-readable medium of claim 1, further comprising:
   instructions for exporting through a filtrate line a filtrate obtained from the filtering step; and
   instructions for detecting blood leakage in the filtrate line to control leakage of blood cells through the filter.

9. The machine-readable medium of claim 1, further comprising:
   instructions for exporting through a filtrate line a filtrate collected from the filtering step;
   instructions for storing the filtrate traveling through the filtrate line in a reservoir;
   instructions for weighing the filtrate stored in the reservoir; and
   instructions for computing the amount of substitution fluid introduced in the blood from the weighing step.

10. The machine-readable medium of claim 1, further comprising:
    instructions for detecting air bubbles from the blood introduced with the substitution fluid; and
    instructions for removing air bubbles from the blood before it is returned into the patient's blood stream.

11. The machine-readable medium of claim 1, further comprising instructions for heating the substitution fluid introduced into the blood to a temperature substantially equal to the patient's body temperature.

* * * * *

UNITED STATES PATENT AND TRADEMARK OFFICE
CERTIFICATE OF CORRECTION

| | |
|---|---|
| PATENT NO. | : 8,795,517 B2 |
| APPLICATION NO. | : 13/960234 |
| DATED | : August 5, 2014 |
| INVENTOR(S) | : Jean-Michel Lannoy |

Page 1 of 1

It is certified that error appears in the above-identified patent and that said Letters Patent is hereby corrected as shown below:

ON THE TITLE PAGE:

Item (71) Applicants:

Please change "Baxter International Inc., Deerfield, IL (US); and Baxter Healthcare S.A. Glattpark (CH)" to --Nikkiso Co., Ltd., Tokyo, Japan--

Signed and Sealed this
Eighteenth Day of November, 2014

Michelle K. Lee
*Deputy Director of the United States Patent and Trademark Office*